US005506212A

United States Patent [19]
Hoke et al.

[11] Patent Number: 5,506,212
[45] Date of Patent: Apr. 9, 1996

[54] OLIGONUCLEOTIDES WITH SUBSTANTIALLY CHIRALLY PURE PHOSPHOROTHIOATE LINKAGES

[75] Inventors: Glenn Hoke, Mt. Airy, Md.; Phillip D. Cook, San Marcos, Calif.

[73] Assignee: ISIS Pharmaceuticals, Inc., Carlsbad, Calif.

[21] Appl. No.: 297,703

[22] Filed: Aug. 29, 1994

Related U.S. Application Data

[63] Continuation of Ser. No. 777,007, Oct. 16, 1991, abandoned, which is a continuation-in-part of Ser. No. 463,358, Jan. 11, 1990, abandoned.

[51] Int. Cl.$^6$ .......................... A61K 31/70; C07H 21/00
[52] U.S. Cl. ................... 514/44; 514/42; 514/43; 514/45; 514/46; 536/24.5; 536/25.33; 536/25.34
[58] Field of Search .................... 514/42, 43, 44, 514/45, 46; 536/24.5, 25.33, 25.34

[56] References Cited

PUBLICATIONS

Androphy, E. J., et al., Bovine papillomavirus E2 trans–activating gene product binds to specific sites in papillomavirus DNA, Nature 325:70–73 (1987).
Amtmann, E. & Sauer, G., Bovine Papillomavirus Virus Transcription: Polyadenylated RNA Species and Assessment of the Direction of Transcription, J. Virol. 43:59–66 (1982).
Baker, C. C. & Howley, P. M., Differential promoter utilization by the bovine papillomavirus in transformed cells and productively infected wart tissues, EMBO J. 6:1027–1035 (1987).
Berg, L. J., et al., Complementation of a Bovine Papilloma Virus Low–Copy–Number Mutant: Evidence for a Temporal Requirement of the Complementing Gene, Mol. Cell. Biol. 6:859–869 (1986).
Boshart, M., et al., A new type of papillomavirus DNA, its presence in genital cancer biopsies and in cell lines derived from cervical cancer, EMBO J. 3:1151–1157 (1984).
Burnett, S., et al., Messenger RNAs from the E1 region of bovine papillomavirus type 1 detected in virus–infected bovine cells, Nucleic Acids Res. 15:8607–8620 (1987).
Chen, E. Y., et al., The primary structure and genetic organization of the bovine papillomavirus type 1 genome, Nature 299:529–534 (1982).
Cowsert, L. M., et al., Topographical and Conformational Epitopes of Bovine Papillomavirus Type 1 Defined by Monoclonal Antibodies, JNCI 79:1053–1057 (1987).
Cowsert, L. M., et al., Identification of the Bovine Papillomavirus L1 Gene Product Using Monoclonal Antibodies, Virology 165:613–615 (1988).
Dahlberg, A. E., et al., Eelectrophoretic Characterization of Bacterial Polyribosomes in Agarose–Acrylamide Composite Gels, J. Mol. Biol. 41:39 (1969).
Dartmann, K., et al., The Nucleotide Sequence and genome Organization of Human Papilloma Virus Type 11, Virology 151:124–130 (1986).
Dürst, M., et al., A papillomavirus DNA from a cervical carcinoma and its prevalence in cancer biopsy samples from different geographic regions, Proc. Natl. Acad. Sci. USA 80:3812–3815 (1983).
DiMaio, D., Nonsense Mutation in Open Reading Frame E2 of Bovine Papillomavirus DNA, J. Virol. 57:475–480 (1986).
DiMaio, D. & Settleman, J., Bovine papillomavirus mutant temperature sensitive for transformation, replication and transctivation, EMBO J. 7:1197–1204 (1988).
Dvoretzky, I. et al., A quantitative in vitro focus assay for bovine papilloma virus, Virology 103:369–375 (1980).
Engel, L. W., et al., Transcriptional Organization of Bovine Papillomavirus Type 1, J. Virol. 47:516–528 (1983).
Frost, E. and Williams, J., Mapping Temperature–Sensitive and Host–Range Mutations of Adenovirus Type 5 by Marker Rescue, Virology 91:39–50 (1978).
Gissmann, L., et al., Human papillomavirus types 6 and 11 DNA seuqences in genital and laryngeal papillomas and in some cervical cancers, Proc. Natl. Acad. Sci. USA 80:560–563 (1983).
Gius, D., et al., Inducible and Constitutive Enhancer Domains in the Noncoding Region of Human Papillomavirus Type 18, J. Virol. 62:665–672 (1988).
Graham, F. L. and van der Eb., A. J., A New technique for the Assay of Infectivity of Human Adenovirus 5 DNA, Virology 52:456–461 (1973).
Groff, D. E. & Lancaster, W. D. Genetic Analysis of the 3' Early Region Transformation and Repliation Functions of Bovine Papillomavirus Type 1, Virology 150:221–230 (1986).
Groman, C. M., et al., Recombinant Genomes Which Express Chloramphenicol Acetyltransferase in Mammalian Cells, Mol. Cell. Biol. 2:1044–1051 (1982).
Heilman, C. A., et al., Virus–Specific Transcription in Bovine Papillomavirus–Transformed Mouse Cells, Virology 119:22–34 (1982).
Herbomel et al., Two Distinct Enhancers with Different Cell Specification Coexist in the Regulatory Region of Polyoma, Cell 39:653 (1984).
Hirochika, H., et al., Enhancers and trans–Acting E2 Transcriptional Factors of Papillomaviruses, J. Virol. 61:2599–2606 (1987).
Iyer, R. P., et al., The Automated Synthesis of Sulfur–Containing Oligodeoxyribonucleotides Using 3H–1,2–Benzodithiol–3–one 1,1 Dioxide as a Sulfure–Transfer Reagent, J. Org. Chem. 55:4693–4699 (1990).

(List continued on next page.)

Primary Examiner—Douglas W. Robinson
Assistant Examiner—James O. Wilson
Attorney, Agent, or Firm—Woodcock, Washburn, Kurtz, Mackiewicz & Norris

[57] ABSTRACT

Sequence specific phosphorothioate oligonucleotides comprising nucleoside units which are joined together by either substantially all Sp or substantially all Rp phosphorothioate intersugar linkages are provided. Such sequence specific phosphorothioate oligonucleotides having substantially chirally pure intersugar linkages are prepared by enzymatic synthesis from nucleoside 5'-O-(1-thiotriphosphates).

6 Claims, No Drawings

PUBLICATIONS

Lambert, P. F., et al., A Transcriptional Repressor Encoded by BPV–1 Shares a Common Carboxy–Terminal Domain with the E2 Transactivator, *Cell* 50:69–78 (1987).

Lusky, M. & Botchan, M. R., Genetic Analysis of Bovine Papillomavirus Type 1 trans–Acting Replicaiton Factors, *J. Virol.* 53:955–965 (1985).

Lusky, M. & Botchan, A Bovine Papillomavirus Type 1–Encoded Modulator Function is Dispensable for Transient Viral Replication but is Required for Establishment of the Stable Palsmid State, M. R., *J. Virol.* 60:729–742 (1986).

Maniatis et al. (Maniatis, T., Fritsch, E. F. and Sambrook, J. *Molecular Cloning: A Laboratory Manual,* Cold Spring Harbor Laboratory, New York, 1982.

McBride, A. A., et al., The carboxy–terminal domain shared by the bovine papillomavirus E2 transactivator and repressor proteins contains a specific DNA binding activity, *EMBO J.* 7:533–539 (1988).

Moskaluk, C. & Bastia, D., The E2 "gene" of bovine papillomavirus encodes an enhancer–binding protein, *Proc. Natl. Acad. Sci. USA* 84:1215–1218 (1987).

Phelps, W. C. et al., The Human Papillomavirus Type 16 E7 Gene Encodes Transactiviation and Transformation Functions Similar to Those of Adenovirus E1A, *Cell* 53:539–547 (1988).

Phelps, W. C. & Howley, P. M., Transcriptional trans–Activation by the Human Papillomavirus Type 16 E2 Gene Product, *J. Virol.* 61:1630–1638 (1987).

Rabson, M. S., et al., Bovine Papillomavirus Type 1 3' Early Region Transformation and Plasmid Maintenance Functions, *J. Virol.* 60:626–634 (1986).

Roberts, J. M. & Weintraub, H., Negative Control of DNA Replication in Composite SV40–Bovine Papilloma Virus Plasmids, *Cell* 46:741–752 (1986).

Sarver, N., et al., Localization and Analysis of Bovine Papillomavirus Type 1 Transforming Functions, *J. Virol.* 52:377–388 (1984).

Spalholz, B. A. et al., Transactivation of a Bovine Papilloma Virus Transcriptional Regularoty Element by the E2 Gene Product, *Cell* 42:183–191 (1985).

Spalholtz et al., Bovine Papillomavirus Transcriptional Regulation: Localization of the E2 Responsive Elements of the Long Control Region, *J. Virol.* 61:2128–2137 (1987).

Spalholz, B. A., et al., Evidence for Cooperativity Between E2 Binding Sites in E2 trans–Regulation of Bovine Papillomavirus Type 1, *J. Virol.,* 62:3143–3150 (1988).

Stenlund, A., et al., Messenger RNAs from the Transforming Region of Bovine Papilloma Virus Type 1, *J. Mol. Biol.* 182:541–554 (1985).

Thierry, F. & Yaniv, M., The BPV1–E2 trans–acting protein can be either an activator or a repressor of the HPV18 regulatory region, *EMBO J.* 6:3391–3397 (1987).

Yang, Y.C., et al., Bovine Papillomavirus Contains Multiple Transforming Genes, *Proc. Natl. Acad. Sci. USA* 82:1030–1034 (1985).

Zur Hausen, H. and Schneider, A., *The Papovaviridae,* vol. 2, pp., 245–264, edited by N. P. Salzman and P. M. Howley, Plenum Press, New York, 1987, The Role of Papillomaviruses in Human Anogenital Cancer.

Cohen, J. S. ed., Oligonucleotides:Antisence Inhibitors of Gene Expression (CRC Press, Inc., Boca Raton, Fla.), p. 111, 1989.

Chin et al., J. Virol., vol. 62, pp. 2994–3002 (1988).

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:1:

GTCCGCGTCC ATGTCGGC											18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:2:

GCTCCCAGGC TCAGATCT											18

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

TGTTGTCGAT AATATTACCA											20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:4:

TTGCTTCCAT CTTCCTCGTC											20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:5:

TCCGTCATCG CTCCTCAGGG											20

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single ( D ) TOPOLOGY: unknown ( i i ) MOLECULE TYPE: DNA (genomic)

( x i ) SEQUENCE DESCRIPTION: SEQ ID NO:6:

TGGGAGCCAT AGCGAGGC                                                                                   18

( 2 ) INFORMATION FOR SEQ ID NO:7:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:7:

GTACTTGCAT AGTCGATCGG AAAATAGGGT TCTCATCTCC CGGGATTTGG TTGAG        55

( 2 ) INFORMATION FOR SEQ ID NO:8:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:8:

CTCAACCAAA TCCCGGGAGA TGAGAACCCT ATTTTCCGAT C                       41

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:9:

CGACTATGCA AGTAC                                                                                       15

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GACTATGCAA GTAC                                                                                        14

OLIGONUCLEOTIDES WITH SUBSTANTIALLY CHIRALLY PURE PHOSPHOROTHIOATE LINKAGES

Portions of this application may have been supported by National Institute of Health Grant No. GM45061.

CROSS REFERENCE TO RELATED APPLICATIONS

This application is a continuation of application Ser. No. 07/777,007, filed Oct. 16, 1991, now abandoned which is a continuation in part of application Ser. No. 07/463,358, filed Jan. 11, 1990, now abandoned.

FIELD OF THE INVENTION

This invention is directed to sequence specific phosphorothioate oligonucleotides comprising nucleosides joined by intersugar linkages and to their synthesis and use. More particularly intersugar linkages linking nucleosides of oligonucleotides of tile present invention are substantially pure all-Sp or all-Rp chiral phosphorothioate linkages. Such oligonucleotides are prepared via enzymatic synthesis. They are especially well suited to diagnostics and research.

BACKGROUND OF THE INVENTION

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in an effort to moderate their disease causing or disease potentiating functions. Recently, however, attempts have been made to moderate the actual production of such proteins by interactions with molecules that direct their synthesis, intracellular RNA. It is the generally object of such therapeutic approaches to interfere with or otherwise modulate gene expression leading to undesired protein formation.

Antisense methodology is the complementary hybridization of relatively short oligonucleotides to single-stranded mRNA or single-stranded DNA such that the normal, essential functions of these intracellular nucleic acids are disrupted. Hybridization is the sequence specific hydrogen bonding of oligonucleotides to Watson-Crick base pairs of RNA or single stranded DNA. Such base pairs are said to be complementary to one another.

Applications of oligonucleotides as diagnostics, research reagents, and potential therapeutic agents requires that the oligonucleotides or oligonucleotide analogs be synthesized in large quantities, be transported across cell membranes, or taken up by cells, appropriately hybridize to targeted RNA or DNA, and subsequently terminate or disrupt nucleic acid function. These critical functions depend partly on the initial stability of oligonucleotides towards nuclease degradation. Further, these functions depend on specificity of the oligonucleotide or oligonucleotide analog for a target molecule.

A serious deficiency of naturally occuring oligonucleotides and existing oligonucleotide analogs for these purposes, particularly those for antisense therapeutics, is the enzymatic degradation of the admininstered oligonucleotide by a variety of ubiquitous nucleolytic enzymes, intracellularly and extracellularly located, hereinafter refered to as "nucleases". It is unlikely that unmodified oligonucleotides will be useful thereapeutic agents because they are rapidly degraded by nucleases. Modification of oligonucleotides to render them resistant to nucleases is therefore greatly desired.

Modifications of oligonucleotides to enhance nuclease resistance has generally taken place on the sugar-phosphate backbone, particularly on the phosphorous atom. Phosphorothioates have been reported to exhibit resistance to nucleases. In addition, phosphorothioate oligonucleotides are generally more chemically stable than natural phosphodiester oligonucleotides. Phosphorothioate oligonucleotides also exhibit solubility in aqueous media. Further, phosphorothioate oligonucleotide-RNA heteroduplexes can serve as substrates for endogenous RNase H. Additionally, phosphorothioate oligonucleotides exhibit high thermodynamic stability. However, while the ability of an antisense oligonucleotide to bind to specific DNA or RNA with fidelity is fundamental to antisense methodology, modifications at the phosphorous oligonucleotides, while exhibiting various degrees of nuclease resistance, have generally suffered from inferior hybridization properties. Cohen, J. S., ed. *Oligonucleotides: Antisense Inhibitors of Gene Expression* (CRC Press, Inc., Boca Raton, Fla. 1989).

One reason for this inferior hybridization may be due to the prochiral nature of the phosphorous atom, modifications on the internal phosphorous atom of modified phosphorous oligonucleotides results in Rp and Sp stereoisomers. Since a practical synthesis of oligonucleotides having substantially all-Rp or all-Sp phosphate intersugar linkages has been unknown, oligonucleotides with modifications at the phosphorous atoms, wherein the resulting molecule has nonsymmetrical substituents, are racemic mixtures having $2^n$ isomers with n equal to the number of phosphorothioate intersugar linkages in the oligonucleotide. Thus a 15-mer phosphorothioate oligonucleotide, containing 14 asymmetric centers has $2^{14}$ or 16,384 diastereomers. In view of this, in a racemic mixture, only a small percentage of the oligonucleotides are likely to hybridize to a target mRNA or DNA with sufficient affinity to be useful in antisense or probe technology.

Attempts to study chemically synthesized phosphorothioate oligonucleotides having chirally pure intersugar linkages has been limited to molecules having only one or two diastereomeric intersugar linkages. The effects of induced chirality in chemically synthesized racemic mixtures of sequence specific phosphorothioate oligonucleotides has not been assessed since synthesis of oligonucleotides having chirally pure intersugar linkages has yet to be accomplished by automated synthesis. This is due to the non-stereospecific incorporation of sulfur during automated synthesis. For example, Stec, W. J., Zon, G. and Uznanski, B., *J. Chromatography*, 326:263 (1985), synthesized certain oligonucleotide phosphorothioates having racemic intersugar linkages; however, they were able to resolve only the diastereomers of certain small oligomers having one or, at most, two diastereomeric phosphorous intersugar linkages.

While chemical synthesis of oligonucleotides having chirally pure intersugar linkages has been limited to either small dimers and trimers or to homopolymers or to, at best, two diastereomeric phosphorous intersugar linkages, the synthesis of phosphorothioates having all-Rp intersugar linkages using enzymatic methods has been investigated by several authors. Burgers, P. M. J. and Eckstein, F., *J. Biological Chemistry*, 254:6889 (1979), and Gupta, A., DeBrosse, C., and Benkovic, S. J. *J. Bio. Chem.*, 256:7689 (1982) enzymatically synthesized diastereomeric polydeoxy-adenylic acid having phosphorothioate intersugar linkages. Brody, R. S. and Frey, P. S., *Biochemistry*, 20:1245 (1981); Eckstein, F. and Jovin, T. M., *Biochemistry,* 2:4546 (1983); Brody, R. S., Adler, S., Modrich, P., Stec, W. J., Leznikowski, Z. J., and Frey, P. A., *Biochemistry,* 21:2570–2572 (1982); and Romaniuk, P. J. and Eckstein, F., *J. Biol. Chem.,* 257:7684–7688 (1982) all enzymatically synthesized poly TpA and poly ApT phosphorothioates while Burgers, P. M. J. and Eckstein, F. *Proc. Natl. Acad. Sci. USA,* 75:4798–4800 (1978) enzymatically synthesized poly UpA phosphorothioates. Cruse, W. B. T., Salisbury, T., Brown, T., Cosstick, R. Eckstein, F. and Kennard, O., *J. Mol. Biol.,* 192:891 (1986), linked three diastereomeric Rp GpC phosphorothioate dimers via natural phosphodiester bonds into a hexamer.

Studies of homopolymeric oligonucleotides which have chirally pure intersugar linkages have indicated that in some cases oligonucleotides having substantially all-Rp intersugar linkages may exhibit greater binding fidelity to target molecules.

The relative ability of an oligonucleotide to bind to complementary nucleic acids may be compared by determining the melting temperature of a particular hybridization complex. The melting temperature ($T_m$), a characteristic physical property of double helixes, denotes the temperature in degrees centigrade at which 50% helical versus coil (unhybridized) forms are present. $T_m$ is measured by using the UV spectrum to determine the formation and breakdown (melting) of hybridization. Base stacking which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$.

In a preliminary report, see Stec, J. W., *Oligonucleotides as Antisense Inhibitors of Gene Expression: Therapeutic Implications.* Meeting abstracts, Jun. 18–21, 1989 thymidine homopolymer octamers having all but one linkage being modified phosphate linkages ("all except one") Rp stereoconfiguration or "all except one" Sp stereoconfiguration in the intersugar linkages were formed from two thymidine methylphosphonate tetrameric diastereomers linked by a natural phosphodiester bond. It was noted that a Rp "all except one" methylphosphonate non-sequence specific thymidine homopolymer octomer, i.e. a $(dT)_8$ mer having all but one Rp intersugar linkage, formed a thermodynamically more stable hybrid (Tm 38° C.) with 15 mer deoxyadenosine homopolymer, i.e. a $d(A)_{15}$ mer, than a hybrid formed by a similar thymidine homopolymer having all-except-one Sp configuration methylphosphonate linkages and of $d(A)_{15}$ mer (Tm <0° C.), i.e. a $d(T)_{15}$ having all but one Sp intersugar linkage. A hybrid between a $(dT)_8$ mer having natural phosphodiester linkages, i.e. octathymidylic acid, and a $d(A)\,l_5$ mer was reported to have a Tm of 14° C.

More recently Ueda, T., Tohda, H., Chikazuni, N., Eckstein, R. and Watanabe, K., *Nucleic Acids Research,* 19:547 (1991), enzymatically synthesized mRNAs intermittently incorporating Rp diastereomeric phosphorothioate linkages for use in translation systems. Ueda, et al. employed T7 coliphane DNA having seventeen promoters and one termination site for T7 RNA polymerase. In vitro synthesis by T7 RNA polymerase produced mRNAs having from several hundred to tens of thousands of nucleotides.

Backbone chirality may also effect the susceptibility of a phosphorothioate oligonucleotide-RNA heteroduplex to serve as a substrate for RNase H activity. The ability to serve as a template for RNAse H will likely have considerable therapeutic importance since it has been suggested that RNAse H may cause a terminating event by cleavage of the RNA component in an RNA-oligonucleotide heteroduplex. With oligonucleotides containing racemic mixtures of Rp and Sp intersugar linkages, it is not known if all phosphorothioate oligonucleotides can function equally as substrates for RNase H. For a variety of catalytic reactions, hydrolysis of the phosphodiester backbone of nucleic acids proceeds by a stereospecific mechanism (an in-line mechanism) and inversion of configuration. Therefore, there may be only a small percentage of oligonucleotides in a racemic mixture that contain the correct chirality for maximum hybridization efficiency and termination of translation by "hybridization arrest". Thus, increasing the percentage of phosphorothioate oligonucleotides that can serve as substrates for RNAse H in a heteroduplex will likely lead to a more efficacious compound for antisense therapy.

To enhance binding fidelity and thus antisense methodology, phosphorothioate oligonucleotides having substantially chirally pure intersugar linkages are greatly desired. Further, such phosphorothioate oligonucleotides having substantially chirally pure intersugar linkages would lead to more efficacious compounds for antisense therapy. However, until now little success has been achieved in an effort to synthesize such molecules. Therefore, simple methods of synthesizing phosphorothioate oligonucleotides having substantially chirally pure intersugar linkages are greatly desired.

BRIEF DESCRIPTION OF THE INVENTION

OBJECTS OF THE INVENTION

In view of the above it is an object of this invention to provide sequence specific phosphorothioate oligonucleotides having substantially chirally pure, either all-Rp or all-Sp intersugar linkages.

It is a further object of this invention to provide phosphorothioate oligonucleotides having all-Rp or all-Sp intersugar linkages that can specifically hybridize to DNA and RNA sequences.

It is an additional object to provide for methods of synthesis of sequence specific phosphorothioate oligonucleotides having substantially chirally pure intersugar linkages.

These and other objects of the present invention shall become apparent to persons skilled in the arts to which this invention pertains given this specification and the claims appended hereto.

SUMMARY OF THE INVENTION

In accordance with this invention phosphorothioate oligonucleotides having all nucleoside units joined together by either substantially all Sp phosphorothioate intersugar linkages or substantially all Rp phosphorothioate intersugar linkages are provided. The phosphorothioate oligonucleotides of the present invention are most preferably complementary to at least a portion of the sequence of targeted RNA or DNA sequence.

Further in accordance with the present invention methods of synthesizing sequence specific phosphorothioate oligonucleotides having substantially chirally pure intersugar linkages are provided wherein said phosphorothioate oligonucleotides are comprised of at least 10 nucleoside units joined together by either substantially all Rp or substantially all Sp intersugar linkages. Preferably, the phosphorothioate oligonucleotides are comprised of from about 10 to about 50 nucleoside units joined by substantially chirally pure intersugar linkages. More preferably, said phosphorothioate oligonucleotides are comprised of from about 15 to about 30 nucleoside units joined by substantially chirally pure intersugar linkages. Most preferably, said phosphorothioate oligonucleotides are comprised of about 12 nucleoside units joined together by substantially chirally pure intersugar linkages. Said methods comprise combining sequence primers, templates, and an excess of all four chirally pure nucleoside 5'-O-(1-thiotriphosphates). Said methods further include synthesizing complementary oligonucleotides by the addition of polymerase followed by cleavage of the primer from the complementary oligonucleotides. In addition, said methods are comprised of disassociating said complementary oligonucleotides from said template.

In alternative embodiments of the present invention methods of synthesizing sequence specific phosphorothioate oligonucleotides having substantially chirally pure intersugar linkages, sequence primers, templates and racemic mixtures of nucleoside 5'-O-(1-thiotriphosphates) are combined. Phosphorothioate oligonucleotides having substantially chirally pure intersugar linkages and which are complementary to the template are synthesized by the addition of polymerase and a selected metal ion. Oligonucleotides thus synthesized are dissassociated from the template and primer.

Phosphorothioate oligonucleotides having substantially chirally pure intersugar linkages are useful to increase the thermodynamic stability of heteroduplexes formed with target RNA and DNA and to elicit RNase H as a termination event. Also phosphorothioate oligonucleotides of the present invention are useful to test for hybridization activity using reporter genes in suitable assays and to test hybridization activity against selected cellular target mRNAs in cultured cells. Further, oligonucleotides of the present invention are useful for modulating the activity of RNA. Methods of modulating the production of protein by an organism are also provided. In addition, methods of treating an animal having a disease characterized by undesired production of protein are set forth.

DETAILED DESCRIPTION OF THE INVENTION

The phosphorous atom in a phosphodiester linkage of an oligonucleotide can be described as being "pro-chiral." Once a non-bonding oxygen atom of the phosphodiester linkage is replaced or modified, a chiral sugar-phosphate linkage is generated. The resulting intersugar linkage is either an Sp intersugar linkage or an Rp intersugar linkage. Replacement of a non-bonding oxygen atom of the natural phosphodiester linkage with sulfur to obtain a phosphorothioate linkage results in the generation of a chiral center and affords Sp and Rp diastereomers. Molecules wherein substantially all of the phosphorous atoms in the sugar backbone are either Sp or Rp, are referred to herein as chirally pure.

Ribonucleoside (NTPeS) and 2'-deoxyribonucleoside (dNTPαS) 5'-O-(1-thiotriphosphates) have been synthesized as Sp and Rp racemic mixtures such as by using the methodology of Ludwig and Eckstein; Ludwig, J. and Eckstein, F., *J. Org. Chem.*, 631–635 (1989). In this exemplary synthetic scheme, unprotected nucleosides can be reacted with 2-chloro-4H-1,3,2 -benzodioxaphosphorin-4-one, which phosphitylates the 5'-hydroxy group. Subsequent reaction with pyrophosphate yields cyclic triphosphate derivatives which are reactive to sulfur, yielding mixtures of Rp and Sp nucleoside 5'-O-(1-thiotriphosphates), i.e alpha-thiotriphosphates. The products can be purified such as by using DEAE-Sephadex chromatography and identified with NMR spectroscopy by characteristic Rp or Sp chemical shifts.

As is shown in the examples below, pure Rp and Sp nucleoside 5'-O-(1-thiotriphosphates) diastereomers can be readily isolated on a preparative scale using, for example, reverse phase HPLC chromatography. Such HPLC isolated nucleotide diastereomers can be further characterized by analytical HPLC comparisons with commercial samples of such Rp and Sp nucleoside 5'-O-(1-thiotriphosphates) diastereomers.

Enzymatic synthesis of sequence specific natural oligonucleotides, i.e. natural phosphodiester oligonucleotides, can be effected by the use of an appropriate nuclease in the presence of a template and primer. In a like manner racemic mixtures of phosphorothioate oligonucleotides having chirally mixed intersugar linkages can be synthesized. According to the teachings of the present invention, such enzymatic synthesis can also be expanded to include the synthesis of sequence specific phosphorothioate oligonucleotides having substantially chirally pure intersugar linkages by utilizing enantiomerically pure all-Sp or all-Rp nucleoside 5'-O-(1-thiotriphosphates) as substrates for appropriate nucleases in the presence of a sequence specific template and a primer. For example, a commercially available DNA polymerase Sequenase™ (U.S. Biochemical, Inc., Cleveland, Ohio) may be used to synthesize phosphorothioate oligonucleotides using a phosphodiester oligonucleotide template and a racemic phosphorothioate oligonucleotide primer. Using this polymerase both phosphodiester and phosphorothioate primers may be extended.

Yields of enzymatically synthesized phosphorothioate oligonucleotides can be optimized by repetitive additions of template and primer, by repetitive additions of polymerase, by repetitive additions of nucleoside triphosphates or by combinations of some or all of these. For instance, repetitive additions of template and primer results in maximizing yields via an enzymatic cascade. Further optimization can be achieved by pre-hybridization of template and primer together in system buffer, followed by cooling and addition of nucleoside triphosphates and polymerase.

Suitable polymerase may be selected to yield either DNA or RNA phosphorothioate oligonucleotides. Such polymerases include but are not necessarily limited to T7 DNA polymerase, modified T7 DNA polymerases such as the above referenced Sequenase, *E. coli* DNA polymerase, DNA poly Klenow fragment polymerase, M. luteus polymerase, T4 bacteriophage polymerase, modified T4 DNA polymerase, T7 RNA polymerase and *E. coli* RNA polymerase.

The enzymatic synthesis proceeds with inversion about the chiral center of the phosphorous atom. Thus use of all-Sp alpha-thiotriphosphates yields substantially all Rp phosphorothioate oligonucleotides while use of all-Rp alpha-thiotriphosphates yields substantially all Sp phosphorothioate oligonucleotides. In an alternate embodiment of the invention phosphorothioate oligonucleotides may be synthesized from Sp-Rp racemic mixtures of nucleoside 5'-O-(1-thiotriphosphates) utilizing metal ions in reaction solutions to promote preferential incorporation of one or the other of the chiral alpha-S-triphosphates. As noted above polymerase synthesis of phosphorothioate oligonucleotide is accomplished with inversion about the chiral center of the precursor nucleoside alpha-S-triphosphate. While not wishing to be bound by theory, it is believed that optimization of an all-Rp configuration may be accomplished by addition of a (relative) high concentration of magnesium ion in the reaction buffer utilizing for instance an *E. coli* polymerase. In a like manner, again while we do not wish to be bound by theory, an all-Sp configuration might be obtained by utilizing a (relative) high manganese ion concentration in the reaction buffer.

In accordance with the present invention, "substantially all" is meant to include all oligonucleotides in which at least 75% of the intersugar linkages are chirally pure. More preferably, oligonucleotides have from about 85% to about 100% chirally pure intersugar linkages are substantially chirally pure. Most preferably, oligonucleotides having from about 95% to about 100% chirally pure intersugar linkages are substantially chirally pure.

For the purposes of this specification and the claims appended hereto the term "phosphorothioate oligonucleotide" includes phosphorothioate oligonucleotides formed from natural occuring bases, sugars and phosphorothioate linkages. Natural bases include adenine, guanine, cytosine, thymine and uracil. Natural sugars include β-D-ribofuranosyl and β-D-2'-deoxy-erythro-pentofuranosyl. To the extent that nucleoside 5'-O-(1-thiotriphosphates) analogs are substrates for suitable polymerases, "phosphorothioate oligonucleotides" also include incorporating modified bases or modified sugars incorporated within the phosphorothioate nucleotide units of the oligonucleotides. Such modified bases and sugars include but are not necessary limited to derivatized bases, derivatized β-D-ribofuranosyl and β-D-2'-deoxy-erythro-pentofuranosyl sugars and carbocyclic pentose sugars.

Phosphorothioate oligonucleotides of the present invention can be contrasted with both natural phosphodiester oligonucleotides and racemic phosphorothioate nucleotides as to their effects on hybridization, nuclease resistance and RNAse H activity.

Homopolymers having all-Rp or all-Sp intersugar linkages have been useful for initial studies of stability and other characteristics, however, these oligomers have little use therapeutically as they are not specific for target molecules. Phosphorothioate oligonucleotides having specific sequences are necessary in order to target specific protein effecting agents.

The sequence specific phosphorothioate oligonucleotides having substantially chirally pure intersugar linkages are thus useful to increase the thermodynamic stability of heteroduplexes with target RNA and DNA and to elicit RNase H as a termination event. Further the phosphorothioate oligonucleotides of the invention are useful to test for hybridization activity using reporter genes in suitable assays and to test hybridization activity against selected cellular target mRNAs in cultured cells.

Radiolabeling can be used to assist with identification of the phosphorothioate oligonucleotide having substantially chirally pure intersugar linkages. For DNA synthesizer synthesized racemate phosphorothioate oligonucleotides, [$^{35}$S] (radio-labeled elemental Sulfur) can be used for oxidation of the hydrogen-phosphonate oligomers obtained from the DNA synthesizer. Labeling of enzymatic synthesized phosphorothioate oligomers can be accomplished such as with [alpha-$^{32}$P]ATP and ligase or [alpha-$^{35}$S]ATPs in the polymerase reaction. Also, radiolabeled nucleoside triphosphates can be used in probe and sequencing analysis. Autoradiograms are prepared in standard manners.

Templates of the present invention are most preferably areas of nucleic acid sequence which direct synthesis of disease potentiating proteins. Short oligonucleotides that base pair to a region of said template oligonucleotide act as primers which form the starting point for oligonucleotide synthesis by polymerases.

Phosphorothioate oligonucleotides having substantially chirally pure intersugar linkages may be synthesized using a primer which may be selected to have a site thereon that is susceptible to nuclease cleavage, as for example restriction endonuclease cleavage. Said cleavage site may be located at the 3'end of said primer. Cleavage at said site by an appropriate restriction endonuclease results in oligonucleotides deriving a first 5'end nucleoside from said primer. Additional nucleosides of said phosphorothioate oligonucleotides of the present invention are those nucleoside chiral thiotriphosphates added via enzymatic means.

By selecting appropriate restriction nucleases in conjunction with selected primers, various 5'-terminal nucleosides of desired phosphorothioate oligonucleotides are appropriately positioned at the 5'end of a phosphorothioate nucleotide. Thus, any endonuclease recognition site can be designed as long as the staggered cut results in one nucleoside from the primer being the first 5'nucleoside of the newly synthesized sequence specific phosphorothioate oligonucleotide of the invention. This results in the generation of different nucleosides on 5'ends of enzymatically synthesized phosphorothioate oligonucleotides of the invention.

Upon completion of enzymatic extension of said primer on an appropriate template of a desired sequence, phosphorothioate oligonucleotides of the invention may be released from said primer by use of appropriate nuclease. For example, for incorporation of a guanosine nucleoside at the 5'end of desired phosphorothioate oligonucleotides, a primer having an CTGCAG sequence at its 3'terminal end may be used. Use of a Pst 1 restriction nuclease then may cleave the A-G linkage. The guanosine nucleoside component of this A-G linkage may thus incorporated as a 5'terminal nucleoside of desired phosphorothioate oligonucleotides. Other restriction endonuclease include but are not limited to BamH1, Smal and Hind III restriction endonucleases.

Oligonucleotides still associated with said template may be disassociated from said template and then purified, for instance by gel electrophoresis and/or chromatography. For example, suitable purification can be accomplished utilizing standard polyacrylamide/urea gel electrophoresis coupled with SepPac (Millipore, Miford, Mass.) chromatography. Other useful chromatographic techniques include HPLC chromatography.

Phosphorothioate oligonucleotides having substantially chirally pure intersugar linkages which are synthesized according to methods of the present invention may be analyzed by a number of methods. For example, configuration analysis of resulting sequence specific phosphorothioate oligonucleotides having substantially chirally pure all-Sp or all-Rp intersugar linkages may be determined by the use of [$_{31}$P] NMR chemical shifts. Such chemical shifts have been used to identify the Rp epimer of a phosphorothioate di-nucleotide. See Ludwig and Eckstein, *J. Org. Chem.,* 631–635 (1989).

The fidelity of sequences of phosphorothioate oligonucleotides of the invention can be determined using the sensitivities of heteroduplexes to S1 nuclease.

The sequence of the phosphorothioate oligonucleotides can be further substatiated by labeling the 3'hydroxyls of phosphorothioate oligonucleotides with [alpha-$^{32}$P] cordycepin triphosphate, i.e. 3'-deoxyadenosine-5'-triphosphate. The resultant oligonucleotides may be subjected to enzymatic degradation.

The relative ability of phosphorothioate oligonucleotides having substantially chirally pure intersugar linkages to bind to complementary strands is compared by determining the melting temperature of a hybridization complex of a phosphorothioate oligonucleotide having substantially chirally pure intersugar linkages and its complementary strand. The melting temperature ($T_m$), a characteristic physical property of double helices, denotes the temperature in degrees centigrade at which 50% helical versus coiled (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non Watson-Crick base pairing has a strong destabilizing effect on the $T_m$. Consequently, as close to optimal fidelity of base pairing as possible is desired to have optimal binding of an oligonucleotide to its targeted RNA.

Phosphorothioate oligonucleotides of the invention can also be evaluated as to their resistance to the degradative ability of a variety of exonucleases and endonucleases. Phosphorothioate oligonucleotides may be treated with nucleases and then analyzed, as for instance, by polyacrylamide gel electrophoresis (PAGE) followed by staining with a suitable stain such as Stains All™ (Sigma Chem. Co., St. Louis, Mo.). Degradation products may be quantitated using laser densitometry.

Fetal calf and human serum can be used to evaluated nucleolytic activity on phosphorothioate oligonucleotides having substantially chirally pure intersugar linkages. For instance a phosphorothioate oligonucleotide having substantially all-Rp intersugar linkages may be evaluated in this manner. Testing on combinations of 3'or 5'end capped (having one or several phosphorothioate linkages per cap) molecules may be used to establish a combination that yields greatest nuclease stability. Capping can be effected by chemically synthesizing the cap portion of a sequence using purified Rp monomers followed by incorporation of said cap into oligonucleotides on the DNA synthesizer. Analysis involving capping can determine the importance of chirality on nucleolytic stability and the number of linkages required to obtain maximum stability.

The sensitivity of phosphorothioate oligonucleotide-RNA heteroduplexes to catalytic activity of RNase H can also be assessed. A phosphorothioate oligonucleotide can be incubated with a radiolabeled target mRNA (synthesized as for instance via T7 RNA polymerase) at various temperatures for hybridization. Heteroduplexes can then be incubated at 37° C. with RNase H from *E. coli* according to the procedure of Minshull, J. and Hunt, T., *Nuc. Acid Res.*, 6433–6451 (1986). Products may then be assessed for RNase H activity by Northern Blot analysis wherein products are electrophoresed on a 1.2% agarose/formaldehyde gel and transferred to nitrocellulose. Filters may then be probed using a random primer [32P]-labeled cDNA complementary to target mRNA and quantitated by autoradiography. Comparisons between different phosphorothioate analogs can be made to determine the impact of chirality on the ability to act as a substrate for RNase H when complexed to RNA.

Comparisons of the susceptibility of heteroduplexes to the catalytic action of *E. coli* RNase H and mammalian RNAse H can be performed. Heteroduplexes can be incubated in rabbit reticulocyte lysates under conditions of translation and assayed via Northern blot analysis for catalytic cleavage of mRNA by endogenous RNase H. This allows for determination of the effects of chirality on mammalian RNAse H activity.

Phosphorothioate oligonucleotides having substantially chirally pure intersugar linkages can also be evaluated for inhibition of gene expression in cell culture model systems. To determine if a phosphorothioate oligonucleotide having substantially pure chirally pure intersugar linkages is more potent or a more specific inhibitor of gene express ion, a phosphorothioate oligonucleotide having substantially chirally pure intersugar linkages designed to target reporter genes may be synthesized and tested in cell culture models of gene expression. The use of the vector pSV2CAT has previously been described to measure effects on gene expression; see Henthorn, P., Zervos, P. , Raducha, M. , Harris, H. , and Kadesch, T. , *Proc. Natl. Acad. Sci. USA*, 85:6342–6346 (1988) . This vector contains the bacterial chloramphenicol acetyl transferase gene under regulatory controls of the SV40 promoter. Utilizing a 15-mer phosphorothioate oligonucleotide having all-Rp intersugar linkages of a sequence complementary to the initiation of translation of the CAT mRNA, pSV2CAT may be transfected into HeLa cells and, following treatment of the cells for 48 hr with a phosphorothioate oligonucleotide having all-Rp intersugar linkages, CAT activity may then be assayed in the cells. The activity of a phosphorothioate having substantially chirally pure intersugar linkages in inhibition of gene expression may then be compared directly with a chemically synthesized random phosphorothioate having diastereomeric intersugar linkages and natural phosphodiester oligonucleotides of the same sequence.

The vector pSV2APAP, see Marcus-Sekura, C. J., Woerner, A. M., Shinozukea, K., Zon,G., Quinnan, G. V. Jr., *Nucleic Acids Research*, 15:5749–5763 (1987), contains the mammalian placental alkaline phosphatase gene (PAP). This can also be used as a reporter for measuring effects on gene expression. PAP has advantages over CAT as a reporter gene in that it is a mammalian gene, rather than a bacterial gene that contains introns and other RNA processing signals. It is presently believed that PAP expression mimics more closely the events in natural mammalian gene expression. A 15-mer phosphorothioate oligonucleotide having substantially chirally pure intersugar linkages as described above for the CAT mRNA can be examined in parallel with chemically synthesized racemic phosphorothioate and natural phosphodiester oligonucleotides having similar sequences. The PAP and CAT reporter constructs are used as controls in reciprocal experiments to test for non-specific effects on gene expression.

Additionally phosphorothioate oligonucleotides having substantially chirally pure intersugar linkages can be evaluated as to their ability to hybridize with RNA. Various areas can be targeted for such hybridization. These areas include but are not limited to herpes virus (HVS), the TAR and TAT regions of HIV, the codon regions of *Candida albicans* chitin synthetase and *Candida albicans* β tubulin, papilloma virus (PAP or HPV), the RAS oncogene and protooncongene, ICAM-1 (intercellular adhesion molecule-1) cytokine and 5'-lipoxygenase. Targeted regions for HVS include GTC CGC GTC CAT GTC GGC (SEQ ID NO:1). Targeted regions for HIV include GCT CCC AGG CTC AGA TCT (SEQ ID NO:2). Targeted regions for *Candida albicans* include TGT TGT CGA TAA TAT TAC CA (SEQ ID NO:3). Targeted regions for human papillomavirus, e.g. virus types HPV-11 and HPV-18, include TTG CTT CCA TCT TCC TCG TC (SEQ ID NO:4). Targeted regions for RAS include TCC GTC ATC GCT CCT CAG GG (SEQ ID NO:5). Targeted regions for ICAM-1 include TGG GAG CCA TAG CGA GGC (SEQ ID NO:6) and the sequence CGA CTA TGC AAG TAC (SEQ ID NO:9) is a useful target sequence for 5'-O-(5-lipoxygenase). In each of the above sequences individual nucleotide units of listed oligonucleotides are list in a 5'to 3'direction from left to right.

In particular, phosphorothioate oligonucleotides of the invention may be used as diagnostics and for research as is specified in copending applications for United States Letters Patents, assigned to the assignee of this invention, and entitled Compositions and Methods for Modulating RNA Activity, Ser. No. 463,358, filed Jan. 1, 1990; Antisense Oligonucleotide Inhibitors of Papilloma Virus, Ser. No. 445,196 Filed Dec. 4, 1989; Oligonucleotide Therapies for Modulating the Effects of Herpesvirus, Ser. No. 485,297, Filed Feb. 26, 1990; Reagents and Methods for Modulating Gene Expression Through RNA Mimicry Ser. No. 497,090, Filed Mar. 21, 1990; Oligonucleotide Modulation of Lipid Metabolism, Ser. No. 516,969, Filed Apr. 30, 1990; Oligonucleotides for Modulating the Effects of Cytomegalovirus Infections, Ser. No. 568,366, Filed Aug. 16, 1990; U.S. Pat. No. 5,166,195, Issued Nov. 24, 1992; Nuclease Resistant Pyrimidine Modified Oligonucleotides for Modulation of Gene Expression, Ser. No. 558,806, Filed Jul. 27, 1990; Novel Polyamine Conjugated Oligonucleotides, Ser. No. 558,663, Filed Jul. 27, 1990; Modulation of Gene Expression Through Interference with RNA Secondary Structure, Ser. No. 518,929, Filed May 4, 1990; Oligonucleotide Modulation of Cell Adhesion, Ser. No. 567,286, Filed Aug. 14, 1990; Inhibition of Influenza Viruses, Ser. No. 567,287, Filed Aug. 14, 1990; Inhibition of Candida, Ser. No. 568, 672, Filed Aug. 16, 1990; and Antisense Oligonucleotide Inhibitors of Papillomavirus, Ser. No. PCT/US90/07067, Filed Dec. 3, 1990. These patents disclose a number of means whereby improved modulation of RNA and DNA activity may be accomplished through oligonucleotide interaction. In that the specific sequences disclosed therein may be used in conjunction with the present invention, the disclosures of the foregoing United States patent applications are incorporated herein by reference.

The following examples are illustrative and are not meant to be limiting of the present invention.

EXAMPLE 1

ISOLATION OF ALL-Sp OR ALL Rp 5'-O-(1-THIOTRIPHOSPHATE) NUCLEOSIDE

5'-O-(1-thiotriphosphate) deoxynucleosides and ribonucleosides are isolated using C-18 reverse phase high performance liquid chromatography (HPLC) using columns packed with ODS Hypersil (Shandon Southern, Runcon, UK) and eluted with an isocratic mixture of solvent A (30 mM potassium phosphate containing 5mM tetrabutylammonium ion, pH 7.0) and solvent B (5 mM tetrabutylammonuium hydroxide in methanol). Alternatively, effective separation is achieved using 100 mM triethylammonium bicarbonate, pH 7.5, containing a linear gradient of acetonitrile from 0% to 15% over 20 minutes.

To establish the purity of such HPLC separated enantiomers the HPLC separated Sp and Rp deoxynucleotide enantiomers are compared to commercially available deoxynucleoside 5'-O-(1-thiotriphosphates) available from E.I. Dupont, Wilmington, Del.

EXAMPLE 2

SYNTHESIS OF PHOSPHOROTHIOATE EXTENSION HAVING SUBSTANTIALLY ALL-Rp INTERSUGAR LINKAGES OF A RACEMIC PHOSPHOROTHIOATE OLIGONUCLEOTIDE

Enzymatic synthesis of an all-Rp phosphorothioate extension of a racemic phosphorothioate oligonucleotide primer is effected using the modified T7 DNA polymerase I, Sequenase™ (U.S. Biochemicals Corp, Cleveland, Ohio). This T7 DNA polymerase is used to extend an 18 mer phosphorothioate oligonucleotide primer hybridized to a 21 mer natural phosphodiester oligonucleotide. 30 picomoles (pmol) of primer and template in a 1×Sequenase™ reaction buffer (U.S. Biochemicals Corp., Cleveland, Ohio) (final vol 10 µl) are heated for 5 minutes at 95° C. and slowly cooled to room temperature. 180 pmol of deoxy 5'-[alpha-$^{35}$S] cytidine triphosphate and Sequenase™ enzyme (U.S. Biochemicals Corp., Cleveland, Ohio) are added and incubated at 37° C. for 20 minutes. The product is analyzed via polyacrylamide gel electrophoresis (PAGE) using a 20% polyacrylamide/7M urea denaturing gel. The autoradiograph of the product is compared to a control reaction absent primer/template. The final product is subjected to further characterization by, for example, enzymatic degradation.. One such degradation is snake venom phosphatase degradation. A snake venom phosphatase degradation of dinucleoside monophosphorothioate synthesized using E. coli DNA polymerase I shows the dinucleoside to be of the Rp configuration.

EXAMPLE 3

SYNTHESIS OF PHOSPHOROTHIOATE CGA CTA TGC AAG TAC (SEQ ID NO:9) OLIGONUCLEOTIDEHAVING SUBSTANTIALLY PURE Rp INTERSUGAR LINKAGES

A large scale enzymatic synthesis of sequence specific all-Rp phosphorothioate oligonucleotide was effected utilizing a 55 mer natural phosphodiester template and a 41 mer natural phosphodiester primer. The template sequence was: GTA CTT GCA TAG TCG ATC GGA AAA TAG GGT TCT CAT CTC CCG GGA TTT GGT TGA G (SEQ ID NO:7). The primer sequence was: CTC AAC CAA ATC CCG GGA GAT GAG AAC CCT ATT TTC CGA TC (SEQ ID NO:8). The template was selected to have a sequence complementary to a desired specific CGA CTA TGC AAG TAC (SEQ ID NO:9) sequence. A Sequenase™ buffer (U.S. Biochemicals Corp., Cleveland, Ohio) diluted from 5× down to 1× was used. The template and primer, both at concentrations of 20nM are added to 40 µL of this buffer. The template and primer were hybridized at 95° C. for 5 minutes and cooled to room temperature. After cooling the buffer was adjusted to 7 mM DTT. 20 µL 1:8 diluted Sequenase™ enzyme and 320 µM each of Sp GTPαS, CTPαS, ATPαS and TTPαS are then added. The reaction solution was adjusted to 140 µL with H$_2$O. It was incubated at 37° C. for 18 hours. The reaction solution was extracted 2× with a like volume of phenol in a standard manner and precipated in a standard manner by treatment with 2.5 volumes of 100% ethanol at −20° C., peltized, washed with 500 µl 70% ethanol, peltized again and dried. The precipitate was suspended in 20 µL H$_2$O for 30 minutes then adjusted to 1 mM CaCl$_2$, 25 mMTris HCl pH 8.0 in 40 µL H$_2$O. The solution was held at 95° C. for 5 minutes and snap cooled, i.e. very quickly cooled with ice. The template and primer were removed from the synthesized oligonucleotide by the addition of 4.6 µM DNase I and incubation at 37° C. for 10 minutes. The reaction mixture was phenol extracted 2× with precipated and precipitated with ethanol as above. The precipate was resuspended in H$_2$O and purfied using 20% polyacrylamide/ 7M urea gel electrophoresis coupled with SepPak™ chromatography (Millipore, Milford, Mass.).

In an alternate synthesis, Pst 1 restriction nuclease (Life Technologies, Inc., Gaithersburg, Md.) was used to cleave the primer-bound phosphorothioate oligonucleotide at the restriction site. The desired CGA CTA TGC AAG TAC phosphorothioate oligonucleotide was purified using polyacrylamide/7M urea gel electrophoresis coupled with Sep-Pak™ chromatography (Millipore, Milford, Mass.). Yields were optimized using enzymatic cascade effected by repetitive template-primer addition throughout the reaction. The cascade augmented synthesis yielded 75 $A_{260}$ units of the CGA CTA TGC AAG TAC all-Rp configuration phosphorothioate oligonucleotide from a 20 ml reaction.

EXAMPLE 4

SYNTHESIS OF PHOSPHOROTHIOATE OLIGONUCLEOTIDES HAVING A RACEMIC MIXTURE OF INTERSUGAR LINKAGES USING AUTOMATED DNA SYNTHESIS.

Oligonucleotides are synthesized on an automated DNA synthesizer (Applied Biosystems model 380B) using hydrogenphosphonate chemistry in a standard manner. See Agrawal, S., Goodchild, J., Civeria, M. P., Thornton, A. H., Sarin, P. S., and Zamecnik, P. C. (1988) *Proc. Natl. Acad. Sci. USA*, 85:7079-7083. After the final coupling step, the phosphorothioate linkages are generated by oxidizing the bound oligomer with sulfur in carbon disulfide/triethylamine/pyridine. After sulfur oxidation, standard deblocking procedures with ammonium hydroxide are used to release the oligonucleotides from the support and remove base blocking groups. The phosphorothioate oligonucleotides are purified by oligonucleotide purification column (OPC; ABI, Foster City, Calif.) chromatography and HPLC, using a Beckman System Gold HPLC. The HPLC-purified oligonucleotides are then precipitated with ethanol and assessed for final purity by gel electrophoresis on 20% acrylamide/7 M urea or by analytical HPLC. The authenticity of the oligonucleotide sequence was assessed by oxidation with iodine in pyridine/water and standard sequencing methods. These oligonucleotides contain a mixture of all possible combinations of Rp and Sp isomers at each phosphorous linkage.

EXAMPLE 5

SYNTHESIS OF COMPLEMENTARY DNA OR RNA SEQUENCES USING T7 RNA POLYMERASE FOR THERMODYNAMIC AND KINETIC HYBRIDIZATION ANALYSIS.

The synthesis of short complementary DNA oligonucleotides of natural phosphodiester linkages was performed utilizing standard automated synthesis on an ABI model 380B DNA Synthesizer. The oligonucleotides of correct length were purified by HPLC and sequenced by standard techniques.

T7 RNA polymerase was use for the synthesis of short, complementary RNA oligonucleotides for hybridization analysis. A large amount of T7 RNA polymerase at high concentrations was needed for the many cycles of initiation required to synthesize short RNAs. Due to this requirement, the T7 RNA polymerase was derived from a strain of *E. coli* that contained a T7 RNA polymerase expression vector, BL21/pAR1219, obtained from Brookhaven National Laboratory (Upton, N.Y.). The isolation yielded approximately 300,000 to 500,000 units of T7 RNA polymerase from 2 l of cells, absorbance value =1.2 $A_{600}$. This was sufficiently concentrated for synthesis of short (10–30 nucleotide) RNA species. For synthesis, a T7 promoter and a template containing the complementary target sequence and T7 promoter hybridization sequence were synthesized using the ABI synthesizer (ABI, Foster City, Calif.). Template and promoter were purified by HPLC to ensure that the correct species was present for enzymatic synthesis. Synthesized products were purified on a 20% polyacrylamide/8M urea gel and sequenced by standard procedures.

EXAMPLE 6

THERMAL DENATURATION

Oligonucleotides (either phosphorothioate oligonucleotides of the invention or otherwise) were incubated with either the complementary DNA or RNA oligonucleotides at a standard concentration of 4 μM for each oligonucleotide in 100 mM ionic strength buffer (89.8 mM NaCl, 10 mM Na-phosphate, pH 7.0, 0.2 mM EDTA). Samples were heated to 90° C. and the initial absorbance taken using a Guilford Response II spectrophotometer (Corning). Samples were then slowly cooled to 15° C and the change in absorbance at 260 nm monitored during the heat denaturation procedure. The temperature was elevated 1 degree/absorbance reading and the denaturation profile analyzed by taking the first derivative of the melting curve. Data was also analyzed using a two-state linear regression analysis to determine the $T_m$ and delta G. The results of these tests are shown in Table 1.

TABLE 1

| THERMAL DENATURATION | | | |
|---|---|---|---|
| SEQUENCE | SEQ ID NO. | COMPLEMENT | $T_m$ |
| Natural Phosphodiester | | | |
| CGA CTA TGC AAG TAC | 9 | DNA | 53.2 |
| CGA CTA TGC AAG TAC | 9 | RNA | 46.2 |
| Phosphorothioate with Racemic Intersugar Linkages | | | |
| CGA CTA TGC AAG TAC | 9 | DNA | 46.0 |
| CGA CTA TGC AAG TAC | 9 | RNA | 36.5 |
| Phosphorothioate with Chirally Pure Intersugar Linkages | | | |
| CGA CTA TGC AAG TAC | 9 | DNA | 45.5 |
| CGA CTA TGC AAG TAC | 9 | RNA | 41.5 |
| GA CTA TGC AAG TAC | 10 | DNA | 44.5 |
| GA CTA TGC AAG TAC | 10 | RNA | 40.0 |

EXAMPLE 7

SYNTHESIS OF RADIOLABELED OLIGONUCLEOTIDES

Filter binding assays are utilized to quantitate the binding stringencies of various phosphorothioate oligonucleotides; that is, their tendencies to hybridize and form heteroduplexes with DNA or RNA. These assays require radiolabeled oligonucleotides.

Phosphorothioate oligonucleotides having all-Rp intersugar linkages are synthesized by enzymatic methods from [35S]-monomers that have been purified from Sp monomers. For automated synthesis of phosphorothioate oligonucleotides containing mixed chirality intersugar linkages, oligonucleotides are synthesized containing hydrogen phosphonates and then sulfurized in the presence of elemental [35S] in a pyridine/carbon disulfide mixture. The resulting radiolabeled phosphorothioate oligonucleotide can be purified by OPC chromatography and HPLC. Target mRNA are applied to nitrocellulose filters and baked at 80° C. for 2 hours, blocked and then hybridized with the radiolabeled phosphorothioate oligonucleotide. Binding stringency is assessed by quantitating radiolabeled oligonucleotide eluted from the filters after increases in temperature or increases in the ionic strength of an eluting buffer, as for instance, Tris NaCl buffer. Eluted oligonucleotides are also assessed for their mobility in an anion exchange HPLC protocol isocratically utilizing phosphate buffer. Results are compared to the mobility of standard oligonucleotides prepared having racemic mixtures of intersugar linkages.

EXAMPLE 8

NUCLEASE DIGESTION

Determination of the rate of nuclease degradation of the phosphorothioate oligonucleotides in media containing 10% fetal calf serum (FCS) was carried out in Dulbecco's Modified Essential Medium (DMEM) containing 10% heat inactivated FCS. Heat inactivation of the FCS was carried out at 55° C. for 1 hour prior to addition to media. Oligonucleotides having racemic and chirally pure intersugar linkages were separately tested for resistance to nuclease digestion. 66 µg/ml of each oligonucleotide were separately added to medium and incubated at 37° C., at the time intervals indicated in Table 2. 15 µl aliquots were removed and added to 15 µl of 9 M urea in 0.1 M Tris-HCl (pH 8.3), 0.1 M boric acid and 2 mM EDTA. Aliquots were mixed by vortex and stored at −20° C. Polyacrylamide gel electrophoresis (PAGE) analysis was on 20% polyacrylamide/7 M urea slab gels. Following electrophoresis, gels were stained using "Stains All" (Sigma Chem. Co., St. Louis, Mo.). Following de-staining, gels were analyzed via laser densitometry using an UltraScan XL device (Pharmacia LKB Biotechnology, Uppsala, Sweden). Integrations were performed and the data presented as the percentage decrease from full length (n) prior to incubation to n-1. These results are shown in Table 2 for the oligonucleotide sequence CGA CTA TGC AAG TAC (SEQ ID NO:9) having Rp-chirally pure intersugar linkages.

TABLE 2

NUCLEASE DIGESTION
Incubation in 10% Fetal Calf Serum
Digestion of
Oligonucleotide of Length n to Length n-1

| Time(Hours) | Phosphorothioate with Racemic Intersugar Linkages | Phosphorothioate with Chirally Pure Intersugar Linkages |
|---|---|---|
| 0 | 0 | 0 |
| 1 | 44 | 10 |
| 2 | 45 | 10 |
| 4 | 54 | 12 |
| 24 | 70 | 44 |
| 48 | 70 | 62 |

As is evident from Table 2, the phosphorothioate oligonucleotide having substantially chirally pure intersugar linkages showed greater resistance to nuclease degradation than did the phosphorothioate oligonucleotide having racemic intersugar linkages.

EXAMPLE 9

RNASE H ANALYSIS

Phosphorothioate oligonucleotides having racemic and substantially chirally pure intersugar linkages were analyzed for suseptibility to RNase H. Oligonucleotides (2-fold molar excess to RNA) and 5 µg (3.1 kb) in vitro synthesized mRNA (using T7 RNA polymerase promoter) were incubated in 5 µl RNase H hybridization buffer for 30 minutes at 60° C. Samples were slowly cooled to room temperature and then adjusted to 3.7 mg/ml BSA, 20 units $E.\ coli$ RNase H (Promega), 142 mMDTT, 150 mM KCl, and 3 mM $MgCl_2$. Samples were incubated for 30 minutes at 37° C. Samples were then phenol extracted, ethanol precipitated, and analyzed by electrophoresis on 1.2% agarose gels following ethidium bromide staining. Markers were run on gels concurrently with the samples to determine approximate length of RNA samples.

EXAMPLE 10

A patient suffering from psoriasis is treated with 10 µg/kg body weight of oligonucleotide sythesized according to the method of Example 3, incorporated in a cream. Daily application of the cream continues until the condition is relieved.

EXAMPLE 11

A patient infected with human papillomavirus HPV11 is treated with oligonucleotide synthesized according to Example 3, having the sequence TTG CTT CCA TCT TCC TCG TC (SEQ ID NO:4). 1000 µg/kg body weight of oligonucleotide is incorporated into a pharmaceutically acceptable carrier and administered by a single intravascular injection, repeated as necessary until the infection is resolved.

EXAMPLE 12

A patient infected with Candida Albicans is treated with oligonucleotide synthesized according to Example 3, having the sequence TGT TGT CGA TAA TAT TAC CA (SEQ ID NO:3). 100 µg/kg body weight doses of oligonucleotide are administered orally in a pharmaceutically acceptable carrier every six hours for one week or until the infection is abated.

We claim:

1. An oligonucleotide represented by SEQ ID NO: 4, wherein at least 75% of the nucleoside units are joined together by Sp phosphorothioate 3' to 5' linkages.

2. An oligonucleotide represented by SEQ ID NO: 4, wherein at least 75% of the nucleoside units are joined together by Rp phosphorothioate 3' to 5' linkages.

3. The oligonucleotide of claim 1, wherein all of the internucleoside linkages are joined together by Sp phosphorothioate 3' to 5' linkages.

4. The oligonucleotide of claim 2, wherein all of the internucleoside linkages are joined together by Rp phosphorothioate 3' to 5' linkages.

5. A composition containing an oligonucleotide of claim 1 and an acceptable carrier.

6. A composition containing an oligonucleotide of claim 2 and an acceptable carrier.

* * * * *

UNITED STATES PATENT AND TRADEMARK OFFICE
CERTIFICATE OF CORRECTION

PATENT NO. : 5,506,212
DATED : April 9, 1996
INVENTOR(S) : Glenn Hoke et al

It is certified that error appears in the above-identified patent and that said Letters Patent is hereby corrected as shown below:

In the Sequence Listing, the following was missing:

(I) Applicant: Hoke, Glenn
(ii) Title of Invention: Chirally Pure Phosphorothioate Oligonucleotides
(iv) Correspondence Address:
    (A) Addressee: John W. Caldwell
    (B) Street:   One Liberty Place, $46^{th}$ Floor
    (C) City, Philadelphia
    (D) State: Pennsylvania
    (E) Country: USA
    (F) Zip: 19103
(v) Computer Readable Form:
    (A) Medium Type: Floppy Disk
    (B) Computer: IBM PC Compatible
    (C) Operating System: PC-DOS/MS-DOS
    (D) Software: PatentIn Release #1.0, Version #1.25
(vi) Current Application Data:
    (A) Application Number:
    (B) Filing Date:
    (C) Classification:
(viii) Attorney/Agent Information
    (A) Name: Caldwell, John W.
    (B) Registration Number: 28,937
    (C) Reference/Docket Number: ISIS-0015
(ix) Telecommunication Information:
    (A) Telephone: 215-568-3100
    (B) Telefax:   215-568-3439

UNITED STATES PATENT AND TRADEMARK OFFICE
CERTIFICATE OF CORRECTION

PATENT NO. : 5,506,212

DATED : April 9, 1996

INVENTOR(S) : Glenn Hoke et al

Page 2 of 4

It is certified that error appears in the above-identified patent and that said Letters Patent is hereby corrected as shown below:

IN THE ABSTRACT:

Last line in the equation "5'-O- (1-thiotriphosphates), the "O" should be underlined Col. 1, line 22, "tile" should be --the--.

Col. 3, line 54 "d(A)1$_5$" should be --d(A)$_{15}$--.

Col. 5, line 19, "5'-O- should be --5'--$\underline{O}$--.

Col. 5, line 57, "(NTPeS)" should be -(NTPαS)-.

Col. 5, line 67, "5'-O-" should be -5'-$\underline{O}$--.

Col. 8, line 9, "3'end" should be written --3' end--.

Col. 8, line 11, "5'end" should be written --5' end--.

Col. 8, line 55, "[$_{31}$ P]" should be --[$^{31}$P]--.

Col. 9, line 57, "[32P] should be --[$^{32}$P]--.

Col. 10, line 8, "express ion" should be --expression--.

Col. 11, line 3, in the equation "5'-O-(5-lipoxygenase)." the "$\underline{O}$" should be underlined.

UNITED STATES PATENT AND TRADEMARK OFFICE
CERTIFICATE OF CORRECTION

PATENT NO.  : 5,506,212

DATED       : April 9, 1996

INVENTOR(S) : Glenn Hoke et al

It is certified that error appears in the above-identified patent and that said Letters Patent is hereby corrected as shown below:

Col. 11, line 5, after "5'" and "3'" there should be a space.

Col. 11, line 11, "Jan.1, 1990" should be --Jan. 11, 1990--.

Col. 11, line 43, in the equation "5'-O-(1-THIOT-" the "O" should be underlined

Col. 11, line 45, in the equation "5'-O-(1-thiotriphosphate)" the "O" should be underlined.

Col. 11, line 59, in the equation "5'-O-(1-thiotriphosphates)" the "O" should be underlined.

UNITED STATES PATENT AND TRADEMARK OFFICE
CERTIFICATE OF CORRECTION

PATENT NO. : 5,506,212

DATED : April 9, 1996

INVENTOR(S) : Glenn Hoke et al

It is certified that error appears in the above-identified patent and that said Letters Patent is hereby corrected as shown below:

Col. 12, line 29, the word "OLIGONUCLEOTIDEHAVING" should be two words --OLIGONUCLEOTIDE HAVING--.

Col. 14, line 62, "[35S]" should be --[$^{35}$S]--.

Col. 14, line 67, "[35S]" should be --[$^{35}$ S].

Col. 16, line 19, "mMDTT" should be --mM DTT--.

Signed and Sealed this

Eighth Day of December, 1998

BRUCE LEHMAN

Attest:

Attesting Officer

Commissioner of Patents and Trademarks